United States Patent

Speranza et al.

Patent Number: 5,030,754
Date of Patent: Jul. 9, 1991

[54] HYDROXY-TERMINATED SUBSTITUTED DIUREA DERIVATIVES

[75] Inventors: George P. Speranza, Austin; Jiang-Jen Lin, Houston, both of Tex.

[73] Assignee: Texaco Chemical Company, White Plains, N.Y.

[21] Appl. No.: 615,101

[22] Filed: Nov. 19, 1990

[51] Int. Cl.$^5$ ............... C07C 275/10; C07C 275/20; C07C 275/32
[52] U.S. Cl. .......................... 564/51; 564/48; 564/50; 564/52; 564/59; 564/60; 560/29; 560/159
[58] Field of Search ............ 564/51, 52, 59, 60, 564/48, 50

[56] References Cited

U.S. PATENT DOCUMENTS

| | | | |
|---|---|---|---|
| 3,364,239 | 1/1968 | Speraza | 564/278 |
| 3,522,304 | 7/1970 | Vogt | 564/48 |
| 3,622,617 | 11/1971 | Windel et al. | 564/52 |
| 3,847,992 | 11/1974 | Moss | 564/479 |
| 4,618,717 | 10/1986 | Renken et al. | 564/475 |

Primary Examiner—Glennon H. Hollrah
Assistant Examiner—S. Kumar
Attorney, Agent, or Firm—Jack H. Park; Kenneth R. Priem; Carl G. Ries

[57] ABSTRACT

Hydroxy-terminated substituted diurea derivatives of hydroxy-terminated polyurea derivatives of secondary monoalkylamines and organic diisocyanates and hydroxy-terminated polyurea derivatives of secondary monoalkylamines and prepolymers of organic diisocyanates with polyoxyalkylene polyols, such as hydroxy-terminated polyurea derivatives of secondary monoalkylamines and organic diisocyanates having the formula:

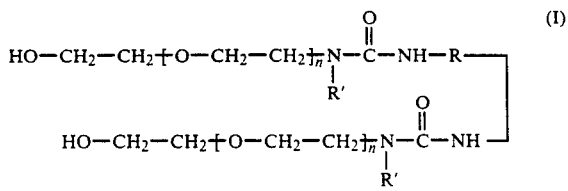

wherein:
R represents an aliphatic or an aromatic group containing from 6 to about 20 carbon atoms,
R' represents H or an alkyl group containing 1 to 6 carbon atoms, and
n is a positive integer having a value of 1 to 4.

6 Claims, No Drawings

HYDROXY-TERMINATED SUBSTITUTED DIUREA DERIVATIVES

BACKGROUND OF THE INVENTION

1. Technical Field of the Invention

This invention relates to hydroxy-terminated polyureas and to a method for their preparation. More particularly, this invention relates to hydroxy-terminated polyureas prepared by reacting an organic diisocyanate with a secondary monoalkylamine derivative of a polyoxyethylene glycol, about 2 moles of the monoalkyl amine derivative being used per mole of organic diisocyanate. This invention also relates to hydroxy-terminated polyurea derivatives of secondary monoalkylamines and prepolymers of organic diisocyanates with polyoxyalkylene polyols. The resultant products are useful in the preparation of polyurea-polyesters and are also useful as polyols for reaction with organic polyisocyanates to prepare polyurethanes.

2. Prior Art

Speranza U.S. Pat. No. 3,364,239 is directed to secondary amino polyalkoxy monoalkanols which are prepared by reacting a primary amino polyalkoxy alkanol with a higher carbonyl compound such as methylethyl ketone, butyraldehyde, etc., to form a Schiff base reaction product which is thereafter hydrogenated in the presence of a hydrogenation catalyst at an elevated temperature and pressure to provide the secondary amino polyalkoxy monoalkanol.

Moss U.S. Pat. No. 3,847,992 discloses a process for partially aminating a polyoxyalkylene polyol by bringing the polyol into contact with a hydrogenation catalyst in the presence of hydrogen and ammonia and a suitable hydrogenation/dehydrogenation catalyst at an elevated temperature and pressure.

Renken et al. U.S. Pat. No. 4,618,717 discloses a process for the conversion of an oxyethylene glycol monoalkyl ether to the corresponding primary amine by reaction with ammonia in the presence of a nickel, copper, chromium-containing catalyst.

Copending U.S. patent application Ser. No. 07/465,660, filed Jan. 16, 1990 entitled "Novel Bis-Hydroxy Diamides and Methods Therefor" discloses a process wherein a polyoxyethylene glycol monoamine is reacted with a dicarboxylic acid in the ratio of about 2 moles of the polyoxyethylene glycol monoamine per mole of dicarboxylic acid. The resultant products have the formula:

$$H-(OCH_2CH_2)_x NH-\overset{O}{\overset{\|}{C}}-R-\overset{O}{\overset{\|}{C}}-NH-(CH_2CH_2O)_x-H$$

Speranza and Lin U.S. Pat. No. 4,927,912, issued May 22, 1990 and entitled "Secondary Isopropyl Amines Derived from Oxyalkylene Diamines and Triamines", discloses a method wherein secondary isopropyl amines are prepared by reacting an oxyethylene and/or an oxypropylene primary diamine or triamine with acetone in the presence of a hydrogenation catalyst and hydrogen.

Copending Speranza and Lin U.S. patent application Ser. No. 07/322,021, filed Mar. 13, 1989, and entitled "Secondary Alkyl Amine Derivatives of Ethylene Diamine" is directed to a method for the preparation of secondary alkyl amine derivatives of ethylene diamine by a continuous process wherein the ethylene diamine is reacted with a methyl alkyl ketone in the presence of a bed of pelleted hydrogenation catalysts and hydrogen.

It is known to prepare substituted ureas by reacting isocyanates with amines. It is also known that isocyanates will react with alcohols to provide urethanes. The reactions described in our invention are very selective. That is, the reaction of the isocyanate takes place exclusively with the hindered amine rather than at the hydroxyl group.

SUMMARY OF THE INVENTION

In accordance with the present invention, hydroxy-terminated substituted diurea derivatives are prepared by reacting a hydroxy-terminated polyoxyethylene monoamine and an organic diisocyanate.

The hydroxy-terminated substituted diurea derivatives of the present invention have the formula:

$$\text{HO}-CH_2-CH_2+O-CH_2-CH_2)_n \overset{\text{R'}}{\underset{|}{N}}-\overset{O}{\overset{\|}{C}}-NH-R \\ \text{HO}-CH_2-CH_2+O-CH_2-CH_2)_n \overset{\text{R'}}{\underset{|}{N}}-\overset{O}{\overset{\|}{C}}-NH \quad (I)$$

wherein:

R represents an aliphatic or an aromatic group containing from 6 to about 20 carbon atoms, R' represents H or an alkyl group containing 1 to 6 carbon atoms, and n is a positive integer having a value of 1 to 4.

The thus-prepared intermediates are useful for a variety of purposes. For example, they may be reacted with dicarboxylic acids to form polyesters. The hydroxy-substituted diurea derivatives can be used alone or in admixture with other polyols such as polyoxypropylene polyols for reaction with organic polyisocyanates to provide a wide variety of polyurethane products such as flexible polyurethane foams, rigid polyurethane foams, and polyurethane elastomers.

DETAILED DESCRIPTION OF THE PRESENT INVENTION

The starting materials for the present invention are primary amine derivatives of polyoxyethylene glycols, $C_1$–$C_6$ alkyl ketones, and organic diisocyanates.

THE POLYOXYALKYLENE GLYCOL AMINE

The polyoxyethylene glycol monoamine starting material should be a compound having the formula:

$$NH_2+CH_2-CH_2-O)_n CH_2-CH_2-OH \quad (IV)$$

wherein n is a positive integer having a value of 1 to 4.

When n has a value of 1, the polyoxyethylene glycol monoamine will be a compound sold commercially by Texaco Chemical Company under the tradename "Diglycol Amine". When n has a value of 2, the product will be a triethylene glycol monoamine and when n has a value of 3, a suitable product is tetraethylene glycol monoamine.

THE METHYL ALKYL KETONE

The methyl alkyl ketone to be used in accordance with the present invention is a ketone having the formula:

(V)

wherein R' represents hydrogen or an alkyl group containing 1 to 6 carbon atoms, and R''' represents methyl.

Examples of suitable methyl alkyl ketones that may be used in the practice of the present invention include acetone, methyl ethyl ketone, methyl n-propyl ketone, methyl isopropyl ketone, methyl n-butyl ketone, methyl isobutyl ketone, etc.

PREPARATION OF THE SECONDARY ALKYL AMINE DERIVATIVE OF THE POLYOXYETHYLENE GLYCOL MONOAMINE

The secondary alkyl amine derivative of the polyoxyethylene glycol monoamine is prepared by reacting the polyoxyalkylene glycol monoamine with the methyl alkyl ketone in the presence of hydroygen and a hydrogenation catalyst.

At least about an equimolar amount of the methyl alkyl ketone and the polyoxyethylene glycol monoamine should be used. However, in order to optimize yield, it is preferable to use an excess of the methyl alkyl ketone. Thus, the ratio of methyl alkyl ketone to polyoxyethylene glycol monoamine may suitably be in the range of about 1:1 to 4:1 and, more preferably, in the range of about 1.2:1 to about 3:1.

THE HYDROGENATION CATALYST

Any suitable pelleted hydrogenation catalyst may be used such as a catalyst comprising one or more of the metals of group VIIIB of the Periodic Table, such as iron, cobalt, nickel, ruthenium, rhodium, palladium, platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 to 85 mole percent of nickel, about 14 to 37 mole percent of copper and about 1 to about 5 mole percent of chromium (as chromia), such as a catalyst disclosed in Moss U.S. Pat. No. 3,151,112 or Yeaky U.S. Pat. No. 3,654,370. As another example, a catalyst of the type disclosed in Boettger et al. U.S. Pat. No. 4,014,933 may be used containing from about 70 to about 95 wt. % of a mixture of cobalt and nickel and from about 5 to about 30 wt. % of iron. As another example, a catalyst of the type disclosed in Habermann U.S. Pat. No. 4,152,353 may be used, such as a catalyst comprising nickel, copper and a third component which may be iron, zinc, zirconium or a mixture thereof, e.g., a catalyst containing from about 20 to about 49 wt. % of nickel, about 36 to about 79 wt. % of copper and about 1 to about 15 wt. % of iron, zinc, zirconium or a mixture thereof.

REACTION CONDITIONS

The reaction should be conducted continuously at a temperature within the range of about 100° to about 300° C., and more preferably at a temperature within the range of about 120° to about 200° C. and at a pressure within the range of about 1000 to about 4000 psig, and more preferably at a pressure within the range of about 2,000 to about 4,000 psig, including a hydrogen partial pressure of about 50 to about 2500 psi, such that there is at least a 50% molar excess of hydrogen in the reactor, based on the ketone.

The reaction should be conducted on a continuous basis, preferably in a reactor containing a bed of a pelleted hydrogenation catalyst and the polyoxyethylene glycol monoamine and the methyl alkyl ketone should not be mixed until just prior to the time when they are charged to the reactor. The feed rate for the mixture of polyoxyethylene glycol monoamine and the methyl alkyl ketone should be within the range of about 0.5 to about 3 w/hr/v.

When the reaction is to be conducted on a continuous basis, the continuous reaction conditions should include a temperature within the range of about 130° to about 180° C., a pressure within the range of about 1000 to about 4000 psig, and a feed rate for the combined mixture of acetone and polyoxyethylene glycol monoamine of about 1 to about 3 w/hr/v when using a preferred nickel, copper, chromia catalyst containing about 60 to about 95 mole percent of nickel, about 14 to about 37 mole percent of copper and about 1 to about 5 mole percent of chromium, as chromia.

THE SECONDARY ALKYL AMINE DERIVATIVE OF THE POLYOXYETHYLENE GLYCOL MONOAMINE

As indicated, the secondary alkyl amine derivative of the polyoxyethylene glycol monoamine is prepared by the reaction of the polyoxyethylene glycol monoamine with the methyl alkyl ketone in the manner described above. The secondary alkyl amine derivative of the polyoxyethylene glycol monoamine will be a compound having the formula:

(III)

wherein R' represents hydrogen or an alkyl group containing 1 to 6 carbon atoms, and
n is a positive integer having a value of 1 to 4.

THE ORGANIC DIISOCYANATE

The organic diisocyanate that is reacted with the secondary alkyl amine derivative of the polyoxyethylene glycol monoamine in accordance with the present invention may be an alkyl diisocyanate or an aromatic diisocyanate.

Suitable aliphatic isocyanates include compounds such as tetramethylene diisocyanate, pentamethylene diisocyanate, hexamethylene diisocyanate, isophorone diisocyanate, etc.

Examples of aromatic isocyanates that may be used include compounds such as m-phenylene diisocyanate, p-phenylene diisocyanate, 2,4-toluene diisocyanate, 2,6-tolylene diisocyanate, bitolylene diisocyanate, naphthalene-1,4-diisocyanate, diphenylene-4,4'-diisocyanate, xylylene-1,4-diisocyanate, xylylene-1,2-diisocyanate, xylylene-1,3-diisocyanate, bis(4-isocyanatophenyl)methane, bis(3-methyl-4-isocyanatophenyl)methane, 4,4'-diphenylpropane diisocyanate, etc.

REACTION CONDITIONS

The reaction between the secondary alkyl amine derivative of the polyoxyethylene glycol monoamine and the organic diisocyanate is suitably conducted in the absence of a catalyst at ambient temperatures and pressures.

minor amount (e.g., 5 to 15 wt. % of ethylene oxide). This can be illustrated for a polyoxypropylene glycol as follows:

$$2O=C=N-R-N=C=O + HO-[CH_2-CH(CH_3)-O]_{n'}-OH \longrightarrow$$

$$O=C=N-R-NH-COO-[CH_2-CH(CH_3)-O]_{n'}-OCO-NH-R-N=C=O$$

THE HYDROXY-TERMINATED SUBSTITUTED DIUREA DERIVATIVE

The hydroxy-terminated substituted diurea derivatives of the present invention are compounds having the formula:

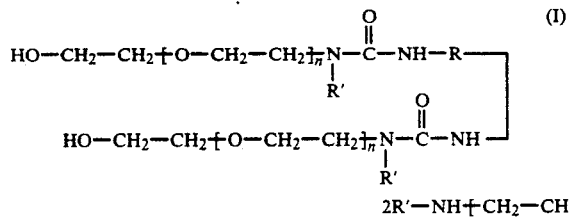

wherein n' represents a positive number having an average value of about 4 to about 100.

HYDROXY-TERMINATED POLYUREA DERIVATIVES OF SECONDARY MONOALKYLAMINES AND PREPOLYMERS OF ORGANIC DIISOCYANATES WITH POLYOXYALKYLENE POLYOLS

The reaction between the secondary monoalkylamine and the prepolymer of the organic diisocyanates with the polyoxypropylene glycol may also be conducted in the absence of a catalyst under ambient conditions of temperature and pressure, i.e.:

$$2R'-NH+CH_2-CH_2-O]_{\overline{n}}CH_2-CH_2-OH + $$

$$O=C=N-R-NH-COO-[CH_2-CH(CH_3)-O]_{n'}-OCO-NH-R-N=C=O \longrightarrow$$

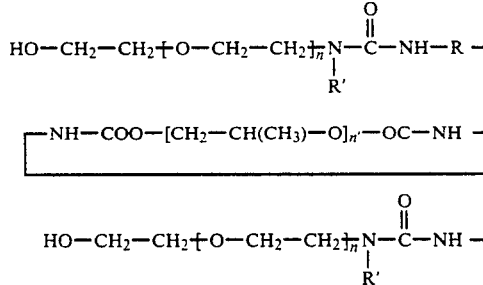

wherein:
R represents an aliphatic or an aromatic group containing from 6 to about 20 carbon atoms,
R' represents hydrogen or an alkyl group containing 1 to 6 carbon atoms, and
n is a positive integer having a value of 1 to 4.

PREPOLYMERS OF THE ORGANIC DIISOCYANATE

The secondary alkyl amine derivative of the polyoxyethylene glycol may also be reacted with a prepolymer of an organic diisocyanate, as described above, in order to convert the prepolymers to the equivalent hydroxy-terminated polyurea derivatives of the prepolymer and the secondary alkyl amine derivative. These products are also useful in the preparation of polyurea-polyesters and polyurethanes.

Prepolymers are prepared by reacting a polyoxyalkylene polyol with a molar excess of the organic diisocyanate in the manner known to those skilled in the art. See, for example, "The Development and Use of Polyurethane Products" by E. N. Doyle (McGraw-Hill Book Company). Thus, for example, an excess of the organic diisocyanate may be reacted with a polyoxypropylene glycol having a molecular weight of about 200 to 6,000 or a hydroxy-ethyl terminated polyol prepared by reacting the polyoxypropylene glycol with a The following examples are given by way of illustration and not as limitations on the scope of this invention, as defined by the appended claims.

WORKING EXAMPLES

EXAMPLE 6310-39

N-Isopropyl derivatives were prepared by allowing acetone to react with the aminoethoxy alcohols and then hydrogenation of the mixture with hydrogen and a metal hydrogenation catalyst. For example, a mixture of aminoethoxyethanol (210 g), acetone (232 g) and a Ni catalyst (25 g) was hydrogenated at 3000 psi. and at 130° C. for four hours in a one liter stirred autoclave. After filtration the N-isopropyl derivative was distilled b.p. 101°–104° C. at 4 mm pressure (212 g). The structure was confirmed by NMR.

EXAMPLE 6310-16: HYDROGENATION OF TEGMA AND ACETONE

Using the similar experimental procedures, the mixture of triethylene glycol monoamine (221 g, 1.5M), acetone (174 g, 3.0M) and a nickel-copper-chromium catalyst (see U.S. Pat. No. 3,151,112) (40 g) was subjected to hydrogenation conditions of 3000 psi hydrogen, 130°–180° C. for about 6 hours. The reaction mixture was filtered and distilled to afford N-isopropyl triethylene glycol monoamine (134° C./4 mm Hg, 213 g), having amine contents of 4.9 meq/g (calc. 5.2 meq/g) and hydroxy number 9.9 meq/g (calc. 10.4 meq/g). The compound was confirmed by NMR.

EXAMPLE 6310-20: HYDROGENATION OF T₄EGMA-ACETONE

Using the similar experimental procedures, the mixture of tetraethylene glycol monoamine (287 g, 1.5M), acetone (174 g, 1.5M) and a nickel catalyst as used in the previous example (40 g) was hydrogenated under conditions of 3000 psi hydrogen at 130° C. for about 4 hours. The product mixture was filtered and distilled to afford N-isopropyl tetraethylene glycol monoamine (133°-135° C./0.75 mm, 259 g), having analyses of 4.20 meq/g for secondary amine (calc. 4.25 meq/g), total amine 4.2 meq/g and hydroxy number 8.1 meq/g (calc. 8.5 meq/g). The structure was confirmed by NMR.

EXAMPLE 6340-88: INTERMEDIATE OF N-ISOPROPYL DGA AND ISOPHORONE DIISOCYANATE ADDUCT

To a 250-ml 3-necked flask equipped with a thermometer, an additional funnel and a stirrer was charged N-isopropyl DGA (44.1 g, 0.30M) and then isophorone diisocyanate was added (33.3 g, 0.15M) dropwise. The mixture was heated to 70°-80° C. for 4 hours. The recovery product was transparent, light colored solid. The H-nmr analysis indicated the following structure:

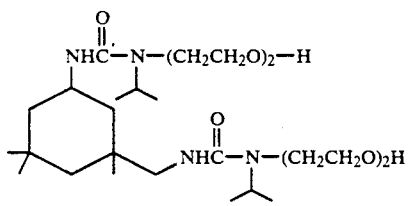

EXAMPLE 6340-89: ADDUCT OF N-ISOPROPYL TEGMA AND IPDI

The similar reaction procedues were used. The mixture of N-isopropyl TEGMA (38.2 g, 0.2M) and IPDI (22.2 g, 1.0M) (exothermic to 35° C.) was heated to 75° C. for 4 hours. The resulting product was very light colored liquid having the following structure:

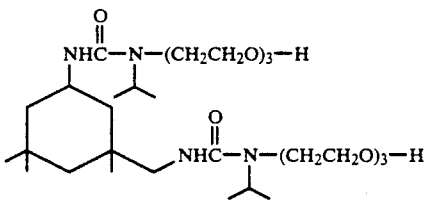

EXAMPLE 6340-90: ADDUCT OF N-ISOPROPYL T₄EGMA AND IPDI

The same reaction procedures except using N-isopropyl T₄EGMA (47 g, 0.2M) and IPDI (22.2 g, 0.1M) produced the product (61 g) as a transparent, light yellow semisolid having the structure:

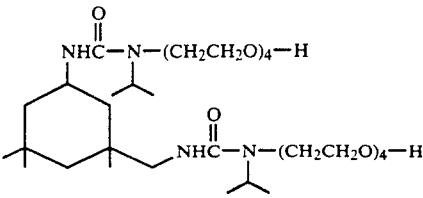

EXAMPLE 6340-96: ADDUCT OF TEGMA AND IPDI

Using triethylene glycol monoamine (TEGMA) instead of N-isopropyl TEGMA (in comparison with example 6340-89), the following experiment was carried out.

To a 250 ml 3-necked flask equipped with a thermometer, an additional funnel, a stirrer and nitrogen-line was charged TEGMA (149 g, 1.0M) then added IPDI (111 g, 0.5M). The mixture was heated to 100° C. for 3 hours. Some gelling was observed. The final product was a yellow solid.

EXAMPLE 6340-91: ADDUCT OF T₄EGMA AND IPDI

To a 500 ml 3-necked flask equipped with a thermometer, an additional funnel, a stirrer and nitrogen-line was charged T₄EGMA (193 g, 1.0M), then added IPDI (111 g, 0.5M) dropwise at 85° C. and kept at 80° C. for 4 hours. The product was a brown semisolid. H-nmr indicated the following structure:

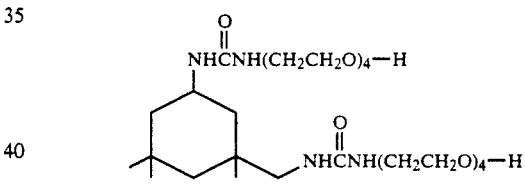

EXAMPLE 6340-96: ADDUCT OF TEGMA AND IPDI

To a 250 ml 3-necked flask equipped with a stirrer, thermometer, nitrogen inlet, now add 149g of triethylene glycol monoamine and 111 g of isophorone diisocyanate. The mixture was heated to 100° C. and held at this temperature for three hours. A small amount of gelling was observed. The final product was a yellow solid.

EXAMPLE 6219-85: TMXDI+T₄EGMA

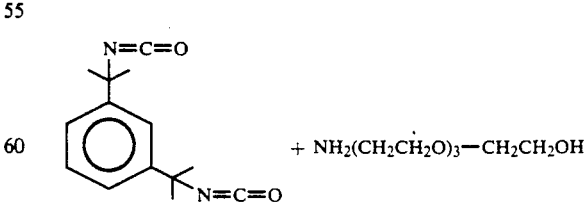

To a one-liter 3-necked flask equipped with a thermometer, stirrer, dropping funnel and a nitrogen inlet was 122 g (0.5M) of TMXDI (from American Cyanamid). Then 193 g (1.0 mole) of tetraethylene glycol monoamine was added over a 50 minute period keeping the temperature below 36° C. A clear viscous product was obtained.

EXAMPLE 6219-88: TMXDI+TEGMA

From 14 g of triethylene glycol monoamine and 122 g of TMXDI in 150 g of isopropanol was obtained 258 g of the bis adduct after the isopropanol was removed. The adduct was a yellow solid.

PREPOLYMER PREPARATION

A prepolymer was prepared by heating two parts of Isonate 143-L (Dow) with one part of polyoxypropylene glycol with a molecular weight of 2000. Isonate 143-L is an aromatic polyisocyanate prepared from methylenediphenyldiisocyanate. To a 100 ml. 3-necked flask equipped with a mechanical stirrer, thermometer, nitrogen inlet and dropping funnel was added 29 g of N-isopropyldiethylene glycol monoamine. Then 27 g of the prepolymer was added over a one hour period while the temperature varied from 29°–37° C. Solids formed to make stirring somewhat difficult so the contents were heated to 90° C. and held for one hour at this temperature. A clear, almost colorless viscous liquid was obtained with terminal hydroxyl groups as expected.

EXAMPLE 6641-79

To a 100 ml flask equipped with a mechanical stirrer and thermometer was added 29 g of N-isopropyl-diglycolamine. Then over a period of one hour was added 27 g of prepolymer from Isonate 143-L and polypropylene glycol-2000. The contents were stirred for one hour after the ingredients were mixed. The contents were heated to 90° C. and held for one hour. Product weighed 55.6 g. All of the isocyanate had reacted and the product was all urea. No urethane was formed. These are NMR observations.

The foregoing examples have been given by way of illustration only and are not intended as limitations on the scope of this invention, which is defined by the appended claims.

We claim:

1. A hydroxy-terminated substituted diurea derivative having the formula:

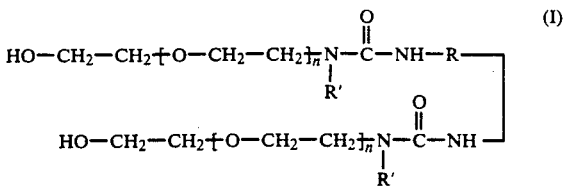

wherein:
R represents an aliphatic or a hydrocarbyl aromatic group containing from 6 to about 20 carbon atoms,
R' represents H or an alkyl group containing 1 to 6 carbon atoms, and
n is a positive integer having a value of 1 to 4.

2. A hydroxy-terminated substituted diurea derivative as in claim 1 wherein R' represent a methyl group.

3. A hydroxy-terminated substituted diurea derivative as in claim 2 wherein R in the formula of claim 1 represents an isophorone group or a tetramethylxylyl group.

4. A hydroxy-terminated substituted diurea derivative as in claim 3 wherein n has a value of 1.

5. A hydroxy-terminated substituted diurea derivative as in claim 3 wherein n has a value of 2.

6. A hydroxy-terminated substituted diurea derivative as in claim 1 wherein R' represents an isopropyl group.

* * * * *